US011208376B2

(12) United States Patent
Wreesmann et al.

(10) Patent No.: US 11,208,376 B2
(45) Date of Patent: Dec. 28, 2021

(54) USE OF A METAL SUPPLEMENT IN ANIMAL FEED

(75) Inventors: Carel Theo Jozef Wreesmann, Lunteren (NL); Adrianus Maria Reichwein, Velp (NL); Marcellinus Alexander Van Doorn, Goor (NL); Javier Martin-Tereso Lopéz, Nijmegen (NL)

(73) Assignee: Nouryon Chemicals International B.V., Arnhem (NL)

(*) Notice: Subject to any disclaimer, the term of this patent is extended or adjusted under 35 U.S.C. 154(b) by 0 days.

(21) Appl. No.: 13/503,237

(22) PCT Filed: Oct. 26, 2010

(86) PCT No.: PCT/EP2010/066187
§ 371 (c)(1),
(2), (4) Date: May 18, 2012

(87) PCT Pub. No.: WO2011/051295
PCT Pub. Date: May 5, 2011

(65) Prior Publication Data
US 2012/0231112 A1    Sep. 13, 2012

Related U.S. Application Data

(60) Provisional application No. 61/256,630, filed on Oct. 30, 2009.

(30) Foreign Application Priority Data

Oct. 30, 2009   (EP) .................................... 09174696

(51) Int. Cl.
| | | |
|---|---|---|
| C07C 229/76 | (2006.01) | |
| A23K 20/22 | (2016.01) | |
| A23K 20/24 | (2016.01) | |
| A23K 20/105 | (2016.01) | |
| A23K 20/20 | (2016.01) | |

(52) U.S. Cl.
CPC .......... *C07C 229/76* (2013.01); *A23K 20/105* (2016.05); *A23K 20/22* (2016.05); *A23K 20/24* (2016.05); *A23K 20/30* (2016.05)

(58) Field of Classification Search
CPC .......... A23L 17/40; A23L 17/65; A23L 17/50; A23L 17/00; A23L 20/30; A61P 3/02; A61P 7/06; A61P 17/14; A61P 9/00; A61P 17/00
USPC .......................................................... 426/2
See application file for complete search history.

(56) References Cited

U.S. PATENT DOCUMENTS

| | | | |
|---|---|---|---|
| 2,960,406 A | * | 11/1960 | Cardon .................. A23K 20/30 426/2 |
| 3,911,117 A | | 10/1975 | Ender |
| 4,040,158 A | | 8/1977 | Payne |
| 5,981,798 A | | 11/1999 | Schonherr et al. |
| 6,960,330 B1 | | 11/2005 | Cox, Jr. |
| 2002/0046427 A1 | | 4/2002 | Nambu et al. |
| 2004/0077714 A1 | | 4/2004 | Abdel-Monem et al. |
| 2008/0096804 A1 | | 4/2008 | Miroshnychenko et al. |

FOREIGN PATENT DOCUMENTS

| | | |
|---|---|---|
| CA | 2 572 311 A1 | 1/2006 |
| EP | 377 526 B1 | 7/1990 |
| EP | 0 968 658 A1 | 1/2000 |
| GB | 1 439 518 | 6/1976 |
| JP | 9-136807 A | 5/1997 |
| JP | 10-175931 A | 6/1998 |
| JP | 2005-058017 A | 3/2005 |
| JP | 2009-149777 A | 7/2009 |
| JP | 2009-155578 A | 7/2009 |
| KR | 10-2005-0051224 A | 6/2005 |
| RU | 2 097 045 01 | 11/1997 |
| RU | 2140971 01 | 11/1999 |
| WO | WO 8301559 A1 * | 5/1983 |
| WO | 96/26999 A1 | 9/1996 |
| WO | WO 97/48773 A1 | 12/1997 |
| WO | WO 00/12463 A1 | 3/2000 |
| WO | WO 2008/137517 A1 | 11/2008 |
| WO | WO 2009/000685 A1 | 12/2008 |
| WO | WO 2009/024518 A1 | 2/2009 |
| WO | WO 2009/071630 A2 | 6/2009 |

(Continued)

OTHER PUBLICATIONS

Trilon M types. BASF the Chemical Company. May 2007.*
"Akzo Nobel introduces a new biodegradable chelating agent". Available online at www.chemserv.com on Oct. 10, 2007.*
"New-Exo-Friendly Chelating Agent: GLDA". Available online at www.essentialingredients.com on Apr. 16, 2009.*
European Search Report for Application No. EP 09 17 4696 dated Dec. 23, 2009.
International Search Report for International Application No. PCT/EP2010/066187 dated Jan. 17, 2011.

(Continued)

*Primary Examiner* — Erik Kashnikow
*Assistant Examiner* — Assaf Zilbering
(74) *Attorney, Agent, or Firm* — Norris McLaughlin, P.A.

(57) ABSTRACT

The invention pertains to the use of a supplement for making metals (nutritionally) available to animals, said supplement comprising at least one compound selected from the group consisting of glutamic acid N,N-diacetic acid (GLDA), a metal complex of GLDA, a sodium salt of GLDA, a potassium salt of GLDA, methylglycine-N,N-diacetic acid (MGDA), a metal complex of MGDA, a sodium salt of MGDA, a potassium salt of MGDA, ethylenediamine N,N'-disuccinic acid (EDDS), a metal complex of EDDS, a sodium salt of EDDS, a potassium salt of EDDS, iminodisuccinic acid (IDS), a metal complex of IDS, a sodium salt of IDS, and a potassium salt of IDS.

18 Claims, No Drawings

(56) References Cited

FOREIGN PATENT DOCUMENTS

WO    WO 2009/103822 A1    8/2009

OTHER PUBLICATIONS

English language abstract for JP 9-136807 A (publication date May 27, 1997).

English language abstract for JP 10-175931 A (publication date Jun. 30, 1998).

English language abstract for RU 2 097 045 C1 A (publication date Nov. 27, 1997).

Apgar et al., "Mineral Balance of Finishing Pigs Fed Copper . . . Growth-Stimulating Levels," J. of Anim. Sci., No. 74 (1996) pp. 1594-1600.

Borowiec et al., "Biodegradation of selected substances . . . of Life Cycle Assessment," Polish Journal of Chemical Technology, 11, 1 (2009) pp. 1-3.

Febles et al., "Phytic Acid Level in Wheat Flours," Journal of Cereal Science 36 (2002) pp. 19-23.

Harland et al., "Phytate: A Good or a Bad Food Component?," Nutrition Research, vol. 15, No. 5 (1995) pp. 773-754.

Wu et al., "Determination of phytic acid in cereals—a brief review," International Journal of Food Science & Technology 44 (2009) pp. 1671-1676.

Japanese Office Action dated Sep. 3, 2013 for Application No. 2012-535792.

English language translation of Japanese Office Action dated Sep. 3, 2013 for Application No. 2012-535792.

English language translation of JP 2009-155578 A published Jul. 16, 2009.

English language translation of JP 2005-058017 A published Mar. 10, 2005.

Seetz, et al.; "GLDA: The New Green Chelating Agent for Detergents & Cosmetics"; (2008); Jornadas-Comite Espanol De La Detergencia; vol. 38; pp. 33-42. Available at https://www.tib.eu/en/search/id/BLSE%3ARN239476026/GLDA-the-new-green-chelating-agent-for-detergents/?tx_tibsearch_search%5Bsearchspace%5D=tn.

"Nitrilotriacetic Acid," Hazardous Substance Fact Sheet, New Jersey Department of Health and Senior Services, Trenton, New Jersey, pp. 1-6 (2001).

Kojdl, "Paper chromatography of metallions on a chelating paper involving α(β)-Alanine-N, N-diacetic acid groups," Chromatographia, vol. 9, No. 8, pp. 401-402, Aug. 1976.

Examination Report issued in the counterpart Australian Application No. 2014201337 dated Jan. 16.

\* cited by examiner

USE OF A METAL SUPPLEMENT IN ANIMAL FEED

This application is a national stage filing under 35 U.S.C. § 371 of PCT/EP2010/066187, filed Oct. 26, 2010, which claims priority to European Patent Application No. 09174696.6, filed Oct. 30, 2009, and U.S. Provisional Patent Application No. 61/256,630, filed on Oct. 30, 2009, the contents of which are incorporated herein by reference in their entirety.

The present invention relates to the use of a supplement for making metals (nutritionally) available to animals. It furthermore relates to animal feed, animal drinking water, or salt licks comprising such a metal supplement, premixes therefor, and to a method of supplementing animal feed, animal drinking water, salt licks, or premixes therefor.

The use of metal sources in animal feed is a long established practice. Copper, zinc, manganese, iron, cobalt, and chromium amongst others are metals which play an important physiological role in animals. Copper deficiency for example results in the failure of pigmentation of hair and wool in numerous animal species. This is especially noticeable in dark coated cattle and sheep. Feathers of turkey poults fed copper-deficient diets also show lack of pigmentation. It can also cause cardiac lesion in cattle, which may even result in sudden death. Furthermore, chicks and pigs fed copper-deficient diets may die suddenly from massive internal haemorrhage due to structural defects in major arteries. Moreover, since copper is essential for the release of iron from the intestinal mucosa and iron storage tissues, copper deficiencies are known to cause anaemia in many species. Intake of adequate amounts of zinc is also important. Signs of zinc deficiency include hair loss, skin lesions, diarrhea, and wasting of body tissues. Accordingly, an adequate level of zinc in the diets of swine, poultry, and cattle has been shown to be important for healthy growth of these animals and increased weight gain. It has furthermore been reported in the literature that animals fed a diet deficient in zinc may tend to develop congenital anomalies and fibrotic changes in the oesophagus. Cobalt is known to be needed for the synthesis of vitamin B12 and manganese and iron play an important role in many enzymatic processes in an animal, i.e. the metal has a catalytic role in the enzymes. Moreover, iron is needed for the haemoglobin function, preventing an iron deficiency in animals will prevent them developing anaemia.

To avoid metal deficiencies in animals, such as deficiencies in copper, manganese, iron or zinc, metal supplements are usually administered to these animals, for example by adding these supplements to their feed.

Providing animals with adequate levels of metal nutrients in their dietary intake is not always as easy as it would seem. The metal should be in a nutritionally available form. For example, dietary supplementation by using conventional salts of zinc, such as zinc chloride, may result in gastrointestinal precipitation into forms which are not available for absorption in the gastrointestinal tract and therefore cannot be used to cover the physiological requirements for these metals. More specifically, the best known factor for gastrointestinal precipitation of trace metals is the presence of phytic acid or phytate in animal feed, though there are other materials that cause a similar undesirable effect in the animal, like tannin, molybdates, phosphates, fibres, and oxalates, hereinafter collectively referred to as "nutritional antagonists," wherein a nutritional antagonist can be defined as any material that decreases the nutritional availability of a nutrient (for example by adsorption, precipitation or by interfering in any of the required steps that lead to the incorporation of metal nutrients into their biological function).

Phytic acid, or phytate when in the salt form, is the principal storage form of phosphorus in many plant tissues. The chemical formula of phytate is depicted below:

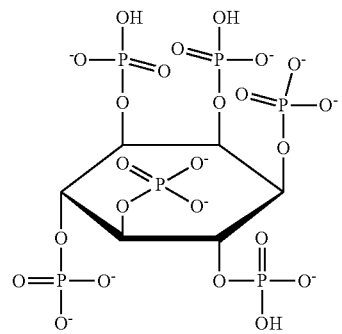

Phytic acid or phytate is present in all feeds of vegetable nature, and is of special quantitative relevance in legumes and grains. It is known to be a strong chelating agent of important metals such as calcium, magnesium, iron, copper, and zinc. It cannot be digested by monogastric animals, the most economically relevant of which are farm animals such as pigs and poultry, and all farmed fish and pets. In the gastrointestinal tract, phytic acid or phytate will give insoluble precipitates of the aforementioned essential trace metals, which greatly inhibits their uptake. Hence, in order to compensate for the potential presence of substances such as phytic acid and phytate in animal diets, high levels of trace metals are normally added to the feed. Metals not taken up by the animal will be excreted and will end up in manure. Eventually, these metals will end up in the soil, and this is considered to be a major long-term environmental threat.

In the literature, many animal feed supplements are described. US 2004/0077714, for example, discloses the use of metal amino acid complexes. More particularly, it discloses the use of metal neutral complexes of one of the essential trace elements such as copper, manganese, and zinc, with di-carboxylic alpha-amino acids such as glutamic acid and aspartic acid.

EP 0377526 relates to a method of supplementing an animal's feed with bioavailable copper, wherein an effective amount of a copper complex salt of an amino acid such as lysine is added to said animal's feed.

However, it was disclosed in for example J. of Anim. Sci. 1996, No 74, pp. 1594-1600, that pigs fed growth-stimulative levels of copper from either $CuSO_4$ or copper lysine complex had similar absorption and retention of copper. Furthermore, it was observed that for the pigs fed copper supplements, the amount of copper in the manure increased considerably.

The presently most used metal supplement to administer zinc to animals is zinc methionine. However, it has been found that this supplement gives a precipitate with phytate, resulting in a non-efficient uptake of the zinc. In order to achieve the required zinc uptake by the animal, relatively high doses are needed, resulting in relatively high zinc levels in manure. The maximum tolerable concentrations for zinc in surface waters and soil will thus easily be exceeded.

It is an object of the present invention to provide for the use of a metal supplement for animals in which the metal will be (nutritionally) available to the animal in a more efficient manner, so that lower levels of metal can be administered, less metal will end up in manure, and, eventually, less metal will end up in the environment.

Furthermore, it is an object of the present invention to provide for the use of a metal supplement for animals with a biodegradable organic part, so that it cannot in itself represent an environmental threat. Finally, it is an object of the present invention to provide for the use of a metal supplement for animals that is readily available, inexpensive, and sustainable, knowing that the major part of the molecule originates from a natural sustainable source.

Surprisingly, it was found that the objectives are met by using specific compounds. More particularly, it was found that the use of metal complexes of EDDS (ethylenediamine N,N'-disuccinic acid), IDS (iminodisuccinic acid), GLDA (glutamic acid-N,N-diacetic acid) or MGDA (methylglycine-N,N-diacetic acid) or the use of sodium or potassium GLDA, GLDA in its acidic form, sodium or potassium MGDA, MGDA in its acidic form, sodium or potassium EDDS, EDDS in its acidic form, or sodium or potassium IDS or IDS in its acidic form results in very good availability of the metal for the animal from the feed, since no precipitate is formed with phytic acid or phytate. Hence, this makes it possible to lower the amount of metal in the animal feed significantly.

Thus, the present invention relates to the use of a supplement for making metals (nutritionally) available to animals, said supplement comprising at least one compound selected from the group consisting of glutamic acid N,N-diacetic acid (GLDA), a metal complex of GLDA, a sodium salt of GLDA, a potassium salt of GLDA, methylglycine-N,N-diacetic acid (MGDA), a metal complex of MGDA, a sodium salt of MGDA, and a potassium salt of MGDA, ethylenediamine N,N'-disuccinic acid (EDDS), a metal complex of EDDS, a sodium salt of EDDS, a potassium salt of EDDS, iminodisuccinic acid (IDS), a metal complex of IDS, a sodium salt of IDS, and a potassium salt of IDS.

Ruminants, such as cattle, appear to have fewer problems with phytate hindering the availability of the just-mentioned mineral metals because the enzyme phytase is present in their alimentary canal. This enzyme will degrade phytate to sugar and phosphate. However, the use of the metal supplement according to this invention has advantages over conventionally used supplements also for those animals, as there are many nutritional antagonists specific to cattle in the gastrointestinal tract of those animals that also influence the availability of metal in animal feed products, as well as other advantages of the metal supplements of the present invention as specified herein.

The present invention also relates to animal feed, animal drinking water, salt licks or premixes therefor comprising (i) at least one compound selected from the group consisting of glutamic acid N,N-diacetic acid (GLDA), a metal complex of GLDA, a sodium salt of GLDA, a potassium salt of GLDA, methylglycine-N,N-diacetic acid (MGDA), a metal complex of MGDA, a sodium salt of MGDA, a potassium salt of MGDA, ethylenediamine N,N'-disuccinic acid (EDDS), a metal complex of EDDS, a sodium salt of EDDS, a potassium salt of EDDS, iminodisuccinic acid (IDS), a metal complex of IDS, a sodium salt of IDS, and a potassium salt of IDS, and (ii) at least one compound of the group of proteins, fats, carbohydrates, minerals, vitamins, vitamin precursors, and water or other edible liquids.

Without being bound or limited by the following theory, we believe that, surprisingly, GLDA, EDDS, IDS, and MGDA form a complex with a metal which is strong enough to survive the passage through the stomach, unlike in the case of weaker chelates such as lysine or methionine complexes of metals. Therefore, it appears that the metal keeps being chelated in the gastrointestinal tract and does not form a complex with the phytate or phytic acid or other nutritional antagonists present in the animal feed, or in other words, using the supplements of the present invention gives the good balance of a chelation of the metal that, on the one hand, is strong enough to make the metal much less susceptible to precipitation with a nutritional antagonist but, on the other hand, is not so strong that the metal is no longer available to the animal to which the supplement is fed. In addition, the metal supplements of the present invention have a satisfactory absorption, affinity, toxicity, and excretion profile.

In this specification the term "protein" encompasses organic compounds made of amino acids; the term "fat" encompasses compounds of fatty acids (chains of carbon and hydrogen atoms, with a carboxylic acid group at one end) bonded to a backbone structure, often glycerol; the term "carbohydrate" encompasses organic compounds comprising mainly carbon, hydrogen, and oxygen atoms, with said atoms present in an about 1:2:1 atom ratio and including the group of saccharides (monosaccharides, disaccharides, oligosaccharides, and polysaccharides, wherein the smaller mono- and di-saccharides are also often referred to as sugars) such as glucose, fructose, sucrose, lactose, glycogen, ribose, and starch; the term "mineral" encompasses compounds, often salts, containing chemical elements other than the four elements carbon, hydrogen, nitrogen, and oxygen present in common organic molecules, such as potassium, chlorine, sodium, calcium, phosphorus, magnesium, zinc, iron, manganese, copper, iodine, selenium, molybdenum, sulfur, cobalt, nickel, chromium, fluorine, and boron; the term "vitamin" encompasses the group of compounds classified by their biological and chemical activity, including the thirteen vitamins presently universally recognized, such as "vitamin A". Precursors of vitamins are well known and cover for example β-carotene. Edible liquids are all liquids known to be edible by animals and cover for example water and liquid fats.

A supplement, also known as a dietary supplement or food supplement or nutritional supplement, is a preparation intended to supplement the diet and provide nutrients that may be missing or may not be consumed in sufficient quantity in a normal diet.

A premix is a mixture containing the supplement in a sufficient amount which, upon mixing with feed, produces an animal feed suitable for feeding an animal the required doses of specific nutrients. Premix usually refers to a substance or object which is mixed in at an early stage in the manufacturing and distribution process. Premixes are thus, often concentrated, compositions composed of a number of animal feed ingredients for blending into commercial rations. Because of the availability of these premixes, for example, a farmer who uses his own grain can formulate his own rations and be assured that his animals are getting the recommended levels of nutrients.

In another embodiment according to the present invention, a metal supplement is used, wherein the supplement comprises at least one anion selected from the group of anions of GLDA, MGDA, EDDS or IDS; and at least one cation selected from the group consisting of calcium, magnesium, copper, zinc, iron, manganese, chromium, and cobalt cations.

If a metal supplement comprising a metal complex of GLDA, MGDA, EDDS or IDS is used, the metal is preferably selected from the group consisting of zinc, copper, iron, manganese, cobalt, chromium, calcium, and magnesium. More preferably, it is zinc, copper, or magnesium.

In another preferred embodiment of the present invention, the metal supplement contains a metal complex or a sodium or potassium salt of MGDA or GLDA.

In a more preferred embodiment the metal supplement comprises a zinc, manganese, iron, or copper complex of GLDA and in a particularly preferred embodiment according to the present invention, the metal supplement comprises a zinc or copper complex of GLDA.

In yet another preferred embodiment, the supplement comprises at least one compound selected from the group consisting of a metal complex of GLDA, with the metal being either calcium or magnesium, a metal complex of MGDA, with the metal being either calcium or magnesium, a metal complex of ethylenediamine N,N'-disuccinic acid (EDDS), with the metal being either calcium or magnesium, a metal complex of iminodisuccinic acid (IDS), with the metal being either calcium or magnesium, sodium GLDA, potassium GLDA, sodium MGDA, potassium MGDA, sodium EDDS, potassium EDDS, sodium IDS, and potassium IDS. Said supplement optionally also comprises one or more salts selected from the group consisting of a copper salt, a zinc salt, an iron salt, a manganese salt, a chromium salt, and a cobalt salt. The calcium and magnesium ions will easily be exchanged for metal ions such as copper ions, zinc ions, iron ions, manganese ions, chromium ions, or cobalt ions which are already present in the animal feed, animal drinking water, or salt licks, or which are added as salts. Sodium GLDA, potassium GLDA, sodium MGDA, or potassium MGDA, sodium EDDS, potassium EDDS, sodium IDS, and potassium IDS will chelate metal ions such as copper ions, zinc ions, iron ions, manganese ions, chromium ions, or cobalt ions which are already present in the animal feed, animal drinking water, or salt licks, or which are added as salts. Thus, metal complexes will be formed in situ, i.e. in the digestive tract of the animal. For dry animal feed products or dry premixes magnesium and calcium complexes are preferred over sodium and potassium salts.

The terms sodium GLDA and potassium GLDA are meant to denote all (partial and full) sodium and potassium salts of GLDA, respectively, and include mixtures of sodium and potassium salts of GLDA or mixed salts of GLDA (i.e. NaxKyHz-GLDA, wherein x+y+z=4). Similarly, the terms sodium and potassium MGDA, EDDS, and IDS are meant to denote all (partial and full) sodium and potassium salts of MGDA, EDDS, and IDS, respectively, and include mixtures of sodium and potassium salts of MGDA, EDDS, and IDS or mixed salts of MGDA (i.e. NaxKyHz-MGDA, wherein x+y+z=3), EDDS (i.e. NaxKyHz-EDDS, wherein x+y+z=4), and IDS (i.e. NaxKyHz-IDS, wherein x+y+z=4). Furthermore, it is also possible to use glutamic acid N,N-diacetic acid (GLDA), methylglycine-N,N-diacetic acid (MGDA), ethylenediamine-N,N'-disuccinic acid (EDDS) or iminodisuccinic acid (IDS) as such in the metal supplement according to the present invention.

The used copper salt is preferably selected from the group consisting of $CuSO_4$, $CuCl_2$, $CuO$, $Cu(OH)_2$, $CuCO_3$, $Cu(NO_3)_2$, $Cu(OH)(HCO_3)$, copper acetate, copper oxalate, copper formate, and copper gluconate. The used zinc salt is preferably selected from the group consisting of $ZnSO_4$, $ZnCl_2$, $ZnO$, $Zn(OH)_2$, $ZnCO_3$, $Zn(NO_3)_2$, zinc acetate, zinc oxalate, zinc formate, and zinc gluconate. The used iron salt is preferably selected from the group consisting of ferric sulfate $(Fe_2[SO_4]_3 \cdot xH_2O)$, ferrous sulfate, ferric pyrophosphate $(Fe_4(P_2O_7)_3 \cdot xH_2O)$, ferric orthophosphate $(FePO_4 \cdot xH_2O)$, sodium iron pyrophosphate $(Fe_4Na_8(P_2O_7)_5 \cdot xH_2O)$, ferric chloride, and ferrous chloride. The manganese salt is preferably selected from the group consisting of $MnSO_4$, $MnCl_2$, and $MnCO_3$. The cobalt salt is preferably selected from the group consisting of $CoCl_2$, $CoSO_4$, and $CoCO_3$.

According to the present invention, the supplement is preferably used in animal feed, animal drinking water, salt licks, or premixes therefor. It is preferably used in animal feed and most preferably in animal feed comprising feedstuff.

In this specification feedstuff is meant to denote any material of an animal or vegetable origin, preferably of a vegetable origin that can be present in animal feed and in one embodiment feedstuff can be chosen from the group of legumes, forages, grain and/or leaves or derivatives thereof, which derivatives are for example obtained by milling the plant-derived materials.

The metal supplement according to the present invention can be used in the feed of a variety of animals. Preferably, it is used in feed for domesticated animals, including companion animals (pets) and aquatic animals (all animals living in an aqueous environment like fish, shrimp, and shell fish). More preferably, it is used in feed for chickens, layers, turkeys, swine, cattle, sheep, goats, horses, cats, dogs, fish, or shrimp.

The metal supplement according to the invention can be used in the animal feed, animal drinking water, salt licks or premixes in any desired concentration. However, because of its improved, much more efficient nutritional availability, it is preferably used in a concentration which is less than half of that of conventionally used metal sources.

The present invention furthermore relates to a metal complex of glutamic acid N,N-diacetic acid (GLDA) or methylglycine-N,N-diacetic acid (MGDA), wherein the metal is selected from the group consisting of copper, zinc, manganese, cobalt, chromium, magnesium, and calcium.

Preferred metal complexes of the invention are $Na_2Cu$-GLDA, $K_2Cu$-GLDA, $H_2Cu$-GLDA, NaKCu-GLDA, NaHCu-GLDA, KHCu-GLDA, $Cu_2$-GLDA, $Na_2Zn$-GLDA, $K_2Zn$-GLDA, $H_2Zn$-GLDA, NaKZn-GLDA, NaHZn-GLDA, KHZn-GLDA, $Zn_2$-GLDA, $Na_2Mn$-GLDA, $K_2Mn$-GLDA, $H_2Mn$-GLDA, NaKMn-GLDA, NaHMn-GLDA, KHMn-GLDA, $Mn_2$-GLDA, NaCu-MGDA, KCu-MGDA, HCu-MGDA, NaZn-MGDA, KZn-MGDA, HZn-MGDA, NaMn-MGDA, KMn-MGDA, HMn-MGDA.

The present invention furthermore relates to a method of supplementing animal feed, animal drinking water, salt licks or premixes therefor, comprising the step of adding a supplement comprising a metal complex of glutamic acid N,N-diacetic acid (GLDA), methylglycine-N,N-diacetic acid (MGDA), ethylenediamine-N,N'-disuccinic acid (EDDS) or iminodisuccinic acid (IDS) to said animal feed, animal drinking water, salt licks or premixes, or by adding at least one compound selected from the group consisting of GLDA, a sodium salt of GLDA, a potassium salt of GLDA, MGDA, a sodium salt of MGDA, a potassium salt of MGDA, EDDS, a sodium salt of EDDS, a potassium salt of EDDS, IDS, a sodium salt of IDS, and a potassium salt of IDS, optionally together with one or more salts selected from the group consisting of a copper salt, zinc salt, an iron salt, a manganese salt, a chromium salt, and a cobalt salt to said animal feed, animal drinking water, salt licks, or premixes.

It should be understood that the addition of the above salt from the group of copper salt, zinc salt, iron salt, chromium salt, manganese salt, and cobalt salt is not needed if copper, zinc, iron, chromium, manganese, and cobalt are already present in the animal feed, animal drinking water, salt licks or premixes.

In another embodiment of the method of the invention, the supplement comprises at least one anion selected from the group of anions of GLDA, MGDA, EDDS or IDS and at least one cation selected from the group consisting of calcium, magnesium, copper, zinc, iron, manganese, chromium, and cobalt cations.

Preferably, in the method in accordance with the invention the supplement comprises a metal complex of GLDA or a metal complex of MGDA In another preferred method the metal is selected from the group consisting of zinc, copper, iron, manganese, cobalt, calcium, and magnesium.

Even more preferably, in the method according to the invention the supplement comprises a zinc, manganese, iron or copper complex of GLDA.

In another embodiment the method concerns supplementing animal feed that in addition comprises a feedstuff from the group of legumes, forages, grain and/or leaves or derivatives thereof.

The method in yet another preferred embodiment involves supplementing feed for domestic animals or aquatic animals, preferably chickens, layers, turkeys, swine, cattle, sheep, goats, horses, cats, dogs, fish, or shrimp.

The present invention is further illustrated by the following non-limiting Examples and Comparative Examples

EXAMPLES

According to P. Wu et al. in *International Journal of Food Science and Technology* 2009, 44, 1671-1676, "phytic acid has a strong ability to form a complex with multivalent metal ions, especially zinc, calcium, and iron. This binding can result in very insoluble salts with poor bioavailability of the minerals." C. I. Febles et al. in *Journal of Cereal Science* 36 (2002) 19-23, remark that "The acid groups present in phytic acid facilitate the formation of several salts, those of the alkaline metals being soluble in water, while divalent metal salts are almost insoluble."

In order to demonstrate the effect of the presence of phytic acid (ex Sigma-Aldrich) on the solubility of various zinc and copper salts, experiments as outlined below were conducted. At 2 different pH-values, i.e. at pH=4 and pH=6, in total 4 zinc and 3 copper salts were combined with a twofold molar excess of phytic acid. The following 3 concentrations of the final metal concentration were tested, i.e. high (H) at 25 mmol/kg, medium (M) at 5 mmol/kg, and low (L) at 0.5 mmol/kg.

Preparation of the Test Solutions

For each concentration and pH a separate phytic acid stock solution was prepared by diluting the calculated amount of phytic acid with de-mineralized water, setting the pH with diluted $NH_4OH$ solutions, and filling up with demineralized water up to the calculated amount. The following 4 phytic acid solutions were prepared in this way:
1. 0.125 mol/kg phytic acid at pH=4
2. 0.125 mol/kg phytic acid at pH=6
3. 0.050 mol/kg phytic acid at pH=4
4. 0.050 mol/kg phytic acid at pH=6

Then the following 2 phytic acid solutions were prepared by diluting the 0.05 M ones. The pH values of these 2 solutions were not adjusted.
5. 0.005 mol/kg phytic acid at pH≈4
6. 0.005 mol/kg phytic acid at pH≈6

The metal complexes and chelates were prepared by weighing an amount of either $ZnSO_4.H_2O$ (35.7% Zn, ex Sigma-Aldrich) or $CuSO_4.5H_2O$ (25.2% Cu, Baker Analyzed (supplier Mallinckrodt Baker B.V.)) and adding the corresponding amount of complexing or chelating agent. A small excess of 2% of the complexing or chelating agent intake was used to prepare the metal-containing solutions. This ensures a complete complexation or chelation of the metal ions. The mixture was dissolved in part of the demineralized water. The pH was adjusted in order to reach a pH value between approximately 4 and 5. All solutions were filled up with demineralized water to 400 g.

The following 4 zinc-containing solutions were prepared in this way.

$ZnSO_4$
  0.125 mol/kg, 9.158 g $ZnSO_4.1H_2O$ were dissolved in de-mineralized water showing a pH of 5.63 and after 1 day some sediment was noticed. With 0.5 M $H_2SO_4$ the pH was reduced to 4.28, after which the solution became clear.

$Zn(Lysine)_2$
  0.125 mol/kg, 9.158 g ZnSO4.1H$_2$O, and 0.255 mol/kg, 18.691 g Lysine (Fluka (supplier Sigma-Aldrich)) were dissolved in demineralized water. Within minutes a clear solution was obtained with a pH of 4.06.

$Zn(Methionine)_2$
  0.125 mol/kg, 9.158 g ZnSO4.1H$_2$O, and 0.255 mol/kg, 15.220 g Methionine (Fluka (supplier Sigma-Aldrich) were dissolved in demineralized water. The pH was adjusted from pH 4.03 to pH 4.51 with $NH_4OH$ 2.5% to obtain a clear solution.

Zn-GLDA-$Na_2$
  0.125 mol/kg, 9.158 g ZnSO4.1H$_2$O, and 0.1275 mol/kg, 36.648 g GL-45-SLA (L-glutamic acid N,N-diacetic acid, tetra sodium salt, Na4-GLDA, Dissolvine GL-45-SLA, ex AkzoNobel). A clear solution was obtained at a pH of 5.27. The pH was not adjusted any further.

The following 3 copper-containing solutions were prepared in the same way.

$CuSO_4$
  0.125 mol/kg, 12.606 g $CuSO_4.5H_2O$ were dissolved in de-mineralized water showing a clear solution with a pH of 3.64. The pH was not adjusted any further.

$Cu(Lysine)_2$
  0.125 mol/kg, 12.609 g $CuSO_4.5H_2O$, and 0.255 mol/kg, 18.686 g Lysine were dissolved in demineralized water. Within minutes a clear solution was obtained with a pH of 2.40. The pH was increased with $NH_4OH$ 2.5% up to pH 4.17.

Cu-GLDA-$Na_2$
  0.125 mol/kg, 12.608 g $CuSO_4.5H_2O$, and 0.1275 mol/kg, 36.619 g GL-45-SLA. A clear solution was obtained at a pH of 5.04. The pH was adjusted to 4.97 with 0.5 M $H_2SO_4$.

Then an equal number of 0.0125 mol/kg solutions were prepared by diluting the above solutions with demineralized water.

This resulted in the following solutions:
7. 0.125 mol/kg $ZnSO_4$
8. 0.0125 mol/kg $ZnSO_4$
9. 0.125 mol/kg $Zn(Lysine)_2$
10. 0.0125 mol/kg $Zn(Lysine)_2$
11. 0.125 mol/kg $Zn(Methionine)_2$
12. 0.0125 mol/kg $Zn(Methionine)_2$
13. 0.125 mol/kg Zn-GLDA-$Na_2$
14. 0.0125 mol/kg Zn-GLDA-$Na_2$ 15. 0.125 mol/kg $CuSO_4$
16. 0.0125 mol/kg $CuSO_4$
17. 0.125 mol/kg $Cu(Lysine)_2$
18. 0.0125 mol/kg $Cu(Lysine)_2$
19. 0.125 mol/kg Cu-GLDA-$Na_2$
20. 0.0125 mol/kg Cu-GLDA-$Na_2$ Combining Metal Salts and Phytic Acid On all 4 zinc-containing and 3 copper-containing solutions in total 6 precipitation tests were carried out, i.e. at levels H, M, and L and for each level at pH=4 and at pH=6. These tests were marked H4, H6, M4, M6, L4, and L6, respectively. In total 42 samples were obtained in this way. After standing for one day the precipitate was removed and the mother liquor was analyzed for its zinc or copper content by FAAS (Flame Atomic Absorption Spectroscopy). The detailed procedure is outlined below.

- 50 ml pre-weighted Greiner tubes were filled with the Phytic acid solutions and the intake exactly determined.
- The metal complex/chelate solutions were added and the intake exactly determined.
- The pH was adjusted with diluted $NH_4OH$ or $H_2SO_4$ solutions.
- Demineralized water was added to a total weight of 50 g and exactly determined.
- The tubes were mixed by hand until homogeneous.
- The tubes were left standing for one day at ambient temperature.
- The tubes were centrifuged when turbidity or sediment was noticed.
- The top layers of the centrifuged tubes and the clear solutions were filtered over a 0.45 µm filter and approximately 12 ml of the filtrate was put in a 15 ml pre-weighted Greiner tube.
- The intake was exactly determined and 1 ml of HNO3 1:1 was added to the solution. The total weight was exactly determined again.

The 50 ml test tubes were filled according to Table 1 below.

TABLE 1

Overview of test sample concentrations (PA = phytic acid)

| Sample code | Test pH | PA stock conc. mol/kg | PA stock intake g | Metal stock conc. mol/kg | Metal stock intake g | PA conc. test sample mmol/kg | Metal conc. test sample mmol/kg |
|---|---|---|---|---|---|---|---|
| H4 | 4 | 0.125 | 20 | 0.125 | 10 | 50 | 25 |
| H6 | 6 | 0.125 | 20 | 0.125 | 10 | 50 | 25 |
| M4 | 4 | 0.05 | 10 | 0.0125 | 20 | 10 | 5 |
| M6 | 6 | 0.05 | 10 | 0.0125 | 20 | 10 | 5 |
| L4 | 4 | 0.005 | 10 | 0.0125 | 2 | 1 | 0.5 |
| L6 | 6 | 0.005 | 10 | 0.0125 | 2 | 1 | 0.5 |

Below the results are given for the zinc and copper concentrations of the mother liquor solutions after analysis by FAAS (Flame atomic absorption measurements).

TABLE 2

Soluble Zn(II) in % (mol/mol) after subjecting complexed or chelated Zn(II) to a two-fold molar excess of phytic acid according to Table 1

| Zinc source | H4 | H6 | M4 | M6 | L4 | L6 |
|---|---|---|---|---|---|---|
| $ZnSO_4$ | 20* | 29* | 51* | 18* | 96 | 58 |
| $Zn(Lysine)_2$ | 22* | 38* | 49* | 14* | 95 | 37 |

TABLE 2-continued

Soluble Zn(II) in % (mol/mol) after subjecting complexed or chelated Zn(II) to a two-fold molar excess of phytic acid according to Table 1

| Zinc source | H4 | H6 | M4 | M6 | L4 | L6 |
|---|---|---|---|---|---|---|
| $Zn(Methionine)_2$ | 21* | 32* | 55* | 13* | 99 | 63 |
| Zn-GLDA-$Na_2$ | 103 | 97 | 97 | 99 | 98 | 98 |

*Sediment or turbidity was noticed in the tube, therefore the tube was centrifuged.

TABLE 3

Soluble Cu(II) in % (mol/mol) after subjecting complexed or chelated Cu(II) to a two-fold molar excess of phytic acid according to Table 1

| Copper source | H4 | H6 | M4 | M6 | L4 | L6 |
|---|---|---|---|---|---|---|
| $CuSO_4$ | 64* | 26* | 97* | 36* | 97 | 80 |
| $Cu(Lysine)_2$ | 103 | 102 | 98 | 98 | 99 | 97 |
| Cu-GLDA-$Na_2$ | 104 | 104 | 99 | 98 | 97 | 99 |

*Sediment or turbidity was noticed in the tube, therefore the tube was centrifuged.

For both zinc and copper GLDA a clear solution was found at all 3 levels. In the case of zinc lysine and zinc methionine immediately a precipitate was formed, just as in the case of all the sulfate salts. In the case of copper-lysine also a clear solution was obtained, but despite a number of attempts copper methionine appeared to be insoluble in water even without the presence of phytate.

Surprisingly, hardly any precipitate at all was formed in the experiments with GLDA.

Unlike the other zinc and copper salts and amino acid complexes, surprisingly only copper-lysine gave rise to a clear solution.

The invention claimed is:

1. A method of making a metal nutritionally available to an animal comprising the step of providing the animal with a supplement incorporated in animal feed, animal drinking water, salt licks, or premixes therefor, wherein the supplement comprises at least one compound selected from the group consisting of glutamic acid N,N-diacetic acid (GLDA), a metal complex of GLDA, a sodium salt of GLDA, a potassium salt of GLDA, methylglycine-N,N-diacetic acid (MGDA), a metal complex of MGDA, a sodium salt of MGDA, and a potassium salt of MGDA.

2. The method according to claim 1 wherein the supplement comprises at least one anion selected from the group of anions of GLDA, or MGDA and at least one cation selected from the group consisting of calcium, magnesium, copper, zinc, iron, manganese, chromium, and cobalt cations.

3. The method according to claim 1, wherein the metal is selected from the group consisting of zinc, copper, iron, manganese, cobalt, chromium, calcium, and magnesium.

4. The method according to claim 1 wherein the supplement comprises a metal complex of GLDA or a metal complex of MGDA.

5. The method according to claim 4 wherein the supplement comprises a zinc, manganese, iron or copper complex of GLDA.

6. The method according to claim 1 wherein the supplement is incorporated in animal feed and the animal feed further comprises a feedstuff from the group of legumes, forages, grain, leaves, or derivatives thereof.

7. The method according to claim 1 wherein the animals are domestic animals or aquatic animals selected from the group consisting of chickens, layers, turkeys, swine, cattle, sheep, goats, horses, cats, dogs, fish, or shrimp.

8. The method according to claim 1 wherein the supplement further comprises at least one compound selected from the group consisting of proteins, fats, carbohydrates, minerals, vitamins, vitamin precursors, and water or other edible liquids.

9. The method according to claim 1 wherein the supplement is chosen from a zinc or copper complex of GLDA.

10. The method according to claim 1 comprising (i) one or more compounds selected from the group consisting of a sodium salt of GLDA, a potassium salt of GLDA, a sodium salt of MGDA, a potassium salt of MGDA, a calcium complex of GLDA, a magnesium complex of GLDA, a calcium complex of MGDA, and a magnesium complex of MGDA; and (ii) one or more salts selected from the group consisting of a copper salt, a zinc salt, an iron salt, a manganese salt, a chromium salt, and a cobalt salt.

11. The method of claim 1 wherein the supplement comprises a metal complex of glutamic acid N,N-diacetic acid (GLDA) or methylglycine-N,N-diacetic acid (MGDA) wherein the metal is selected from the group consisting of copper, manganese, chromium, cobalt, magnesium, and calcium.

12. The method of claim 11 wherein the complex is $Na_2$Cu-GLDA, $K_2$Cu-GLDA, $H_2$Cu-GLDA, NaKCu-GLDA, NaHCu-GLDA, KHCu-GLDA, $Cu_2$-GLDA, $Na_2$Zn-GLDA, $K_2$Zn-GLDA, $H_2$Zn-GLDA, NaKZn-GLDA, NaHZn-GLDA, KHZn-GLDA, $Zn_2$-GLDA, $Na_2$Mn-GLDA, $K_2$Mn-GLDA, $H_2$Mn-GLDA, NaKMn-GLDA, NaHMn-GLDA, KHMn-GLDA, $Mn_2$-GLDA, NaCu-MGDA, KCu-MGDA, HCu-MGDA, NaZn-MGDA, KZn-MGDA, HZn-MGDA, NaMn-MGDA, KMn-MGDA, or HMn-MGDA.

13. The method of claim 1 comprising a step of adding the supplement to animal feed, animal drinking water, salt licks or premixes, wherein the supplement comprises (i) a metal complex of glutamic acid N,N-diacetic acid (GLDA) or methylglycine-N,N-diacetic acid (MGDA), or (ii) at least one compound selected from the group consisting of GLDA, a sodium salt of GLDA, a potassium salt of GLDA, MGDA, a sodium salt of MGDA, a potassium salt of MGDA.

14. The method of claim 1, wherein the animal feed, animal drinking water, salt licks, or premixes therefor comprises the metal.

15. The method of claim 14, wherein the animal feed, animal drinking water, salt licks, or premixes therefor has a reduced amount of the metal compared to animal feed, animal drinking water, salt licks, or premixes therefor that does not have the supplement.

16. The method of claim 1, wherein the animal has a nutritional need for the metal.

17. The method of claim 1, wherein the animal is provided with an effective amount of the supplement to make the metal nutritionally available to the animal.

18. The method of claim 13 wherein one or more salts selected from the group consisting of a copper salt, a zinc salt, an iron salt, a manganese salt, a chromium salt, and a cobalt salt is added to the animal feed, animal drinking water, salt licks or premixes along with the supplement.

* * * * *